United States Patent [19]

Young et al.

[11] Patent Number: 5,320,941
[45] Date of Patent: Jun. 14, 1994

[54] DNA SEQUENCE ENCODING MAS ONHCOGENE, POLYPEPTIDES ENCODED THEREFROM AND DIAGNOSTIC AND OTHER METHODS BASED THEREFROM

[76] Inventors: Dallan Young, 64 Central St., Huntington, N.Y. 11743; Michael H. Wigler, 2 Halyard Ct., Cold Spring Harbor, N.Y. 11724; Ottavio Fasano, Meyerhofstrasse, 1-D6900 Heidelberg RFA, Fed. Rep. of Germany

[21] Appl. No.: 872,087

[22] Filed: Jun. 6, 1986

[51] Int. Cl.$^5$ ............... G01N 33/574; G01N 33/535
[52] U.S. Cl. ..................... 435/7.23; 435/7.9; 435/960; 435/6; 436/813
[58] Field of Search .......... 435/7, 7.23, 960, 6; 436/501, 504, 515, 542, 64, 813

[56] References Cited

U.S. PATENT DOCUMENTS

| | | | |
|---|---|---|---|
| 4,311,688 | 1/1982 | Burchiel et al. | 436/547 |
| 4,559,311 | 12/1985 | Stenman et al. | 436/813 X |
| 4,584,278 | 4/1986 | Knauf | 436/813 X |
| 4,686,180 | 8/1987 | Coggin, Jr. et al. | 436/813 X |

OTHER PUBLICATIONS

Chemical Abstracts 101 (11), 1984, pp. 318–319, #86901h, Cline et al., "Oncogene Detection".

*Primary Examiner*—Esther M. Kepplinger

[57] ABSTRACT

This invention provides a DNA sequence comprising an activated oncogene, said oncogene encoding a polypeptide capable of transforming NIH3T3 cells and of inducing a tumor when injected into nude mice, said DNA sequence having a nucleotide sequence substantially as shown in FIGS. 3A and 3B.

The invention also concerns a polypeptide molecule encoded by an activated oncogene, said molecule having the properties of transforming NIH3T3 cells and of inducing a tumor when injected into nude mice and further said polypeptide having an amino acid sequence substantially as shown in FIGS. 3A and 3B.

Finally, this invention provides a method for treating a tumor induced by an activated mas oncogene.

23 Claims, 6 Drawing Sheets

```
                                        GGATCCAGAAGGGTCATTCAATCAGTTCTC
AGTCTTATCAGGTCTAAGTTCCTTTCTTATCAGGTCCTAAAGGCCTAATCTTATCATTGTGACAAAGATAACTGTAGAG
TCTGTTAAACTTTTTTTTTAATAACATGAAGATTATGATTTATAGCTGAATTTCTCCCTTTTATTCCAATTCAACAATT
TTCATGGCTTTTTGTGTTTGTTTTGTTCTGGACATATTTACAGAAAATTACCTGAAGAGTTCCAACCTGAGGCCTCCTC

ATG GAT GGG TCA AAC GTG ACA TCA TTT GTT GTT GAG GAA CCC ACG AAC ATC TCA ACT GGC
MET Asp Gly Ser Asn Val Thr Ser Phe Val Val Glu Glu Pro Thr Asn Ile Ser Thr Gly    20

AGG AAC GCC TCA GTC GGG AAT GCA CAT CGG CAA ATC CCC ATC GTG CAC TGG GTC ATT ATG
Arg Asn Ala Ser Val Gly Asn Ala His Arg Gln Ile Pro Ile Val His Trp Val Ile MET    40

AGC ATC TCC CCA GTG GGG TTT GTT GAG AAT GGG ATT CTC CTC TGG TTC CTG TGC TTC CGG
Ser Ile Ser Pro Val Gly Phe Val Glu Asn Gly Ile Leu Leu Trp Phe Leu Cys Phe Arg    60

ATG AGA AGA AAT CCC TTC ACT GTC TAC ATC ACC CAC CTG TCT ATC GCA GAC ATC TCA CTG
MET Arg Arg Asn Pro Phe Thr Val Tyr Ile Thr His Leu Ser Ile Ala Asp Ile Ser Leu    80

CTC TTC TGT ATT TTC ATC TTG TCT ATC GAC TAT GCT TTA GAT TAT GAG CTT TCT TCT GGC
Leu Phe Cys Ile Phe Ile Leu Ser Ile Asp Tyr Ala Leu Asp Tyr Glu Leu Ser Ser Gly    100

CAT TAC TAC ACA ATT GTC ACA TTA TCA GTG ACT TTT CTG TTT GGC TAC AAC ACG GGC CTC
His Tyr Tyr Thr Ile Val Thr Leu Ser Val Thr Phe Leu Phe Gly Tyr Asn Thr Gly Leu    120

TAT CTG CTG ACG GCC ATT AGT GTG GAG AGG TGC CTG TCA GTC CTT TAC CCC ATC TGG TAC
Tyr Leu Leu Thr Ala Ile Ser Val Glu Arg Cys Leu Ser Val Leu Tyr Pro Ile Trp Tyr    140

CGA TGC CAT CGC CCC AAG TAC CAG TCG GCA TTG GTC TGT GCC CTT CTG TGG GCT CTT TCT
Arg Cys His Arg Pro Lys Tyr Gln Ser Ala Leu Val Cys Ala Leu Leu Trp Ala Leu Ser    160

TGC TTG GTG ACC ACC ATG GAG TAT GTC ATG TGC ATC GAC AGA GAA GAA GAG AGT CAC TCT
Cys Leu Val Thr Thr MET Glu Tyr Val MET Cys Ile Asp Arg Glu Glu Glu Ser His Ser    180

CGG AAT GAC TGC CGA GCA GTC ATC ATC TTT ATA GCC ATC CTG AGC TTC CTG GTC TTC ACG
Arg Asn Asp Cys Arg Ala Val Ile Ile Phe Ile Ala Ile Leu Ser Phe Leu Val Phe Thr    200

CCC CTC ATG CTG GTG TCC AGC ACC ATC TTG GTG GTG AAG ATC CGG AAG AAC ACG TGG GCT
Pro Leu MET Leu Val Ser Ser Thr Ile Leu Val Val Lys Ile Arg Lys Asn Thr Trp Ala    220

TCC CAT TCC TCC AAG CTT TAC ATA GTC ATC ATG GTC ACC ATC ATT ATA TTC CTC ATC TTC
Ser His Ser Ser Lys Leu Tyr Ile Val Ile MET Val Thr Ile Ile Ile Phe Leu Ile Phe    240

GCT ATC CCC ATG AGA CTC CTT TAC CTG CTG TAC TAT GAG TAT TGG TCG ACC TTT GGG AAC
Ala MET Pro MET Arg Leu Leu Tyr Leu Leu Tyr Tyr Glu Tyr Trp Ser Thr Phe Gly Asn    260

CTA CAC CAC ATT TCC CTG CTC TTC TCC ACA ATC AAC AGT AGC GCC AAC CCT TTC ATT TAC
Leu His His Ile Ser Leu Leu Phe Ser Thr Ile Asn Ser Ser Ala Asn Pro Phe Ile Tyr    280

TTC TTT GTG GGA AGC AGT AAG AAG AGA TTC AAG GAG TCC TTA AAA GTT GTT CTG ACC
Phe Phe Val Gly Ser Ser Lys Lys Lys Arg Phe Lys Glu Ser Leu Lys Val Val Leu Thr    300

AGG GCT TTC AAA GAT GAA ATG CAA CCT CGG CGC CAG AAA GAC AAT TGT AAT ACG GTC ACA
Arg Ala Phe Lys Asp Glu MET Gln Pro Arg Arg Gln Lys Asp Asn Cys Asn Thr Val Thr    320

GTT GAG ACT GTC GTC TAA GAACTGTGAGGGAAGTTGTGGATAAAAATGGTGGAACACAGGTCATTTTTAGTTT
Val Glu Thr Val Val ...                                                             325

GTGCTTGGAATATGACTTAAGTATCTCCTAAATGTGATACAGAAGAACATCTCATCCCATATGCATGAGATACTAATTA

ATGATGAAA
```

```
                                GGATCCAGAAGGTCATTCAATCAGTTCTC
AGTCTTATCAGGTCTAAGTTCCTTTCTTATCAGTTCCTAAAGGCCTAATCTTATCATTGTGACAAAGATAACTGTAGAG
TCTGTTAAACTTTTTTTAATAACATGAAGATTATGATTTATAGCTGAATTTCTCCCTTTATTCCAATTCAACAATT
TTCATGGCTTTTGTGTTTGTTTGTTCTGGACATATTACAGAAAATTACCTGAAGAGTTCCAACCTGAGGCCTCCTC

ATG GAT GGG TCA AAC GTG ACA TCA TTT GTT GTT GAG GAA CCC ACG AAC ATC TCA ACT GGC     20
MET Asp Gly Ser Asn Val Thr Ser Phe Val Val Glu Glu Pro Thr Asn Ile Ser Thr Gly

AGG AAC GCC TCA GTC GGG AAT CAT GCA ATC CGG CAA CAT CCC ATC GTG CAC TGG GTC ATT ATG  40
Arg Asn Ala Ser Val Gly Asn His Ala Ile Arg Gln His Pro Ile Val His Trp Val Ile MET

AGC ATC TCC CCA GTG GGG TTT GTT GAG AAT GGG ATT CTC CTG TGC TTC CGG              60
Ser Ile Ser Pro Val Gly Phe Val Glu Asn Gly Ile Leu Leu Cys Phe Arg

ATG AGA AGA AAT CCC TAC GTC TTC ACT ATC ACC CAC CTG TCT ATC GCA GAC ATC TCA CTG     80
MET Arg Arg Asn Pro Tyr Val Phe Thr Ile Thr His Leu Ser Ile Ala Asp Ile Ser Leu

CTC TTC TGT ATT TTC ATC TTG TCT TTA GCT TAT GAT TAT GAG CTT TCT TCT GGC            100
Leu Phe Cys Ile Phe Ile Leu Ser Leu Ala Tyr Asp Tyr Glu Leu Ser Ser Gly

CAT TAC TAC ACA ATT GTC ACA TTA TCA GTG ACT TTT CTG TTT GGC TAC AAC ACG GGC CTC    120
His Tyr Tyr Thr Ile Val Thr Leu Ser Val Thr Phe Leu Phe Gly Tyr Asn Thr Gly Leu

TAT CTG ACG ATT AGT GAG AGG TGC GTC CTT TAC GTC CTT TAC CCC ATC TGG TAC            140
Tyr Leu Thr Ile Ser Glu Arg Cys Val Leu Tyr Val Leu Tyr Pro Ile Trp Tyr

CGA TGC CAT CGC CCC AAG TAC CAG TCG GCA TTG GTC TGT GCC CTT CTG TGG GCT CTT TCT   160
Arg Cys His Arg Pro Lys Tyr Gln Ser Ala Leu Val Cys Ala Leu Leu Trp Ala Leu Ser
```

FIG. 3A

```
TGC TTG GTG ACC ACC ATG GAG TAT GTC ATG TGC ATC GAC AGA GAA GAG AGT C

DNA SEQUENCE ENCODING MAS ONHCOGENE, POLYPEPTIDES ENCODED THEREFROM AND DIAGNOSTIC AND OTHER METHODS BASED THEREFROM

BACKGROUND OF THE INVENTION

This work was supported by grants from the American Cancer Society, American Business for Cancer Research Foundation and the National Institutes of Health. The U.S. Government has certain rights in this invention.

Throughout this application various publications are referenced by arabic numerals within parentheses. Full citations for these references may be found at the end of the specification immediately preceding the claims. The disclosures of these publications in their entireties are hereby incorporated by reference into this application in order to more fully describe the state of the art as known to those skilled therein as of the date of the invention described and claimed herein.

The first oncogenes discovered were the transforming genes of the oncogene viruses (3). The subsequent discovery that the oncogenes of retroviruses were derived from normal host cellular genes provided the first direct evidence that cellular genomes contain genes with transforming potential. More recently, the development of techniques for DNA transfer in eucaryotic cells led to the discovery of cellular transforming genes in tumor cells by their ability to induce foci of transformed NIH3T3 cells (30). Several new oncogenes have been discovered this way, including N-ras (43), met (7), neu (1) and possibly others (19, 31, 46).

To search for oncogenes which may not be capable of detection by the focus induction assay, a sensitive new bioassay for transforming genes based on the tumorigenicity in nude mice of NIH3T3 cells following cotransfection with a selectable marker and DNA from tumor cells has been employed. Using this assay, three transforming genes were derived from the DNA of the MCF-7 cell line (14). A new human oncogene called mas which was detected by the tumorigenicity assay following cotransfection with DNA isolated from a human epidermoid carcinoma is described. This gene efficiently induces tumorigenicity and has a weak focus inducing activity in NIH3T3 cells. cDNAs containing the entire coding sequence of have been cloned. The mas gene encodes a protein with seven hydrophobic regions that are potential transmembrane domains, suggesting that mas is an integral membrane protein. The structure of mas protein is unique among cellular oncoproteins and may represent a new functional class.

SUMMARY OF THE INVENTION

The invention concerns a DNA sequence comprising an activated oncogene which encodes a polypeptide capable of transforming NIH3T3 cells and of inducing a tumor when injected into nude mice, said DNA sequence having a nucleotide sequence substantially as shown in FIGS. 3A and 3B.

This invention also concerns methods for detecting tumor cells which comprise isolating genomic DNA or RNA from a cell, contacting the DNA or RNA so isolated with a detectable marker which binds specifically to at least a portion of the sequence encoding an activated oncogene of this invention, or to at least a portion of the RNA sequence encoded by an activated oncogene of this invention, and detecting the marker so bound, the presence of bound marker indicating the presence of a tumor cell.

This invention also concerns a method of determining the predisposition of a subject to a disease, which comprises isolating the genomic DNA or RNA from a cell from the subject, contacting the DNA or RNA so isolated with a detectable marker which specifically binds to at least a portion of an activated oncogene of this invention, or to a portion of the RNA encoded by an activated oncogene of this invention, and detecting the marker so bound, the presence of bound marker indicating a predisposition of the subject to the disease.

The invention also concerns a polypeptide molecule encoded by an activated oncogene, said polypeptide having the properties of transforming NIH3T3 cells, inducing a tumor when injected into nude mice, and further said polypeptide having an amino acid sequence substantially as shown in FIGS. 3A and 3B.

Tumor cells and tumors expressing the polypeptide of this invention may be detected with a detectable marker which specifically binds to at least a portion of the polypeptide of this invention. Further, subjects predisposed to diseases associated with the polypeptide of this invention may be identified with a detectable marker which specifically binds to at least a portion of the polypeptide.

Methods for detecting a tumor or tumor cells comprise isolating serum from a subject, contacting the serum with a detectable marker which binds specifically to at least a portion of a polypeptide of this invention to form a marker-polypeptide complex, and detecting the marker so bound, the presence of bound marker indicating the presence of a tumor.

Finally, the invention concerns a method for treating in a subject a tumor induced by an activated mas oncogene which comprises isolating an immunoglobulin molecule which specifically binds at least a portion of a polypeptide encoded by the activated mas oncogene, attaching to the immunoglobulin molecule so isolated a substance which substantially limits the growth of a tumor or which destroys tumors to produce an antitumor immunoglobulin molecule, and contacting the tumor with an effective amount of the antitumor immunoglobulin molecule so produced, thereby limiting tumor growth or destroying the tumor.

BRIEF DESCRIPTION OF THE FIGURES

FIGS. 3A-3B. Nucleotide sequence of coding and flanking regions of the mas gene. The DNA sequence was derived from cDNA clones and the genomic subclone pMS422. The amino acid sequence deduced from the coding region is shown above the DNA sequence. The inframe stop codons of the open reading frame are indicated by asterisks. The DNA sequence from the 14th nucleotide position 5' from the start ATG to the 3' end was derived from the cDNA clones. The sequence of the coding and 5' regions were determined from the genomic clone pMS422. The numbers on the right are amino acid coordinates.

DETAILED DESCRIPTION OF THE INVENTION

Figure 1:
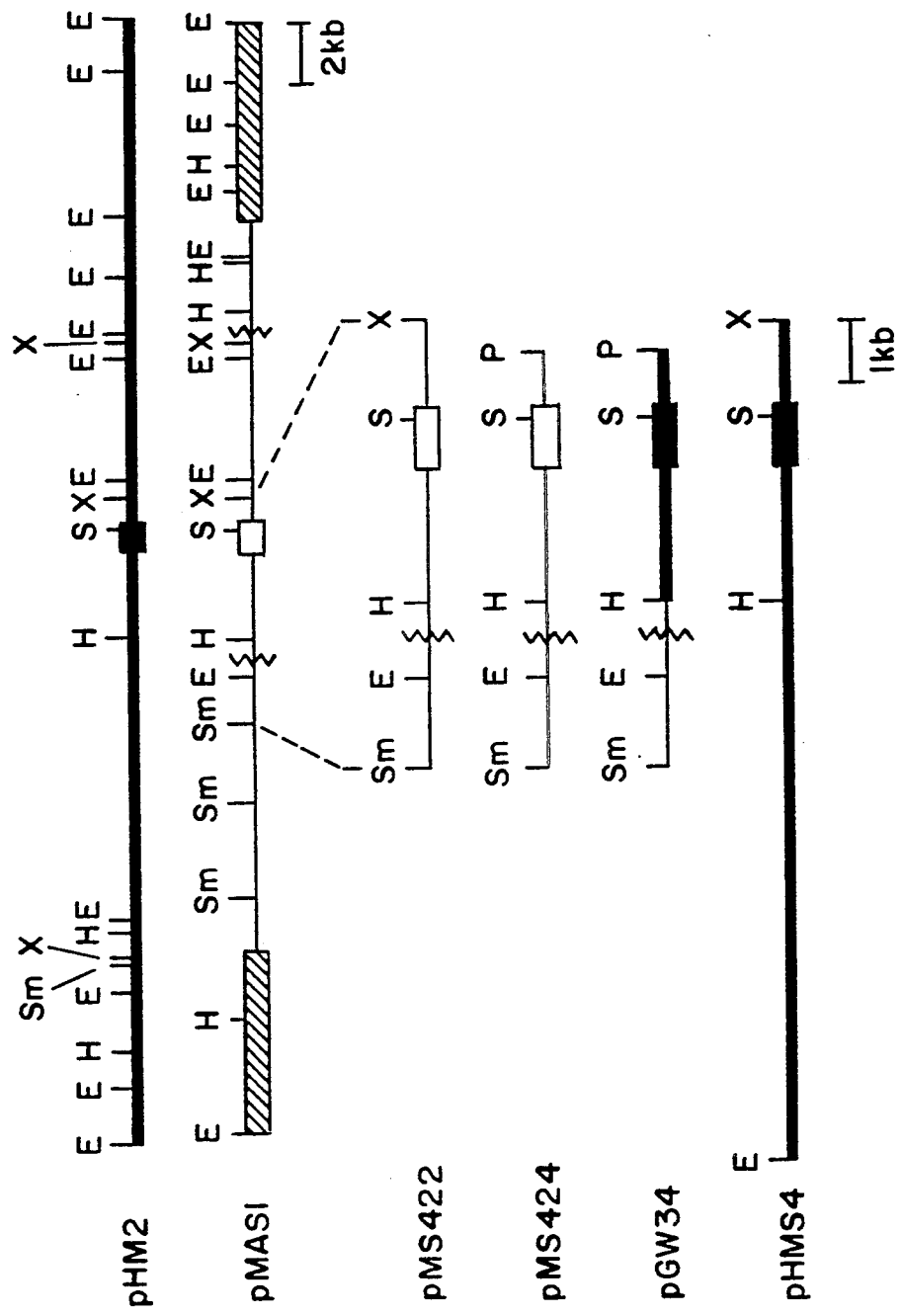
FIG. 1. Maps of restriction endonuclease sites in mas clones. Filled boxes and thick lines indicate the coding region and flanking sequences derived from the placental mas allele. Open boxes and thin lines indicate the coding region and flanking sequences derived from the rearranged mas allele. The hatched areas indicate regions containing mouse repetitive DNA. Squiggles indicate the sites of DNA rearrangements. Restriction sites are indicated by the letters E (EcoRI), H (HpaI), S (SalI), Sm (SmaI), P (PstI), X (XholI).

A DNA sequence comprising an activated oncogene has been isolated which encodes an polypeptide capable of transforming NIH3T3 cells and of inducing a tumor when injected into nude mice. The DNA sequence has a nucleotide sequence substantially as shown in FIGS. 3A and 3B.

The DNA sequence of this invention encodes a oncogene. The sequence may be isolated from a variety of sources, although the presently preferred sequence encodes the human mas gene. The polypeptide produced by the transcription of the gene and the translation of the gene product will vary with the initial DNA sequence.

A method of detecting a tumor cell which contains the DNA sequence of this invention is described. The method comprises isolating genomic DNA from a cell, contacting the DNA isolated from the cell with a detectable marker which binds specifically to at least a portion of the DNA sequence of this invention which encodes an activated oncogene and detecting the marker so bound. The presence of bound marker indicates the presence of a tumor cell.

The detectable marker may be a labelled DNA sequence, including a labelled cDNA sequence, having a nucleotide sequence complementary to at least a portion of the DNA sequence of this invention, produced by methods known to those skilled in the subject art.

The detectable marker may also be a labelled ribonucleotide (RNA) sequence having a nucleotide sequence complementary to at least a portion of the DNA sequence of this invention, and may be isolated by methods known to those skilled in the art. Detectable markers of this invention will be labelled with commonly employed radioactive labels, i.e. $^{32}P$, although other labels may be employed. The markers will be detected by autoradiographic, spectrophotometric or other means known in the art.

A method of detecting a tumor cell which contains RNA encoded by a DNA sequence of this invention is described. The method comprises isolating RNA from a cell, contacting the RNA isolated from the cell with a detectable marker which binds specifically to at least a portion of the RNA encoded by an activated oncogene and detecting the marker so bound. The presence of bound marker indicates the presence of a tumor cell.

The detectable marker may be a labelled DNA sequence, including a labelled cDNA sequence, having a nucleotide sequence complementary to at least a portion of the DNA sequence of this invention, produced by methods known to those skilled in the subject art.

The detectable marker may also be a labelled ribonucleotide (RNA) sequence having a nucleotide sequence complementary to at least a portion of the DNA sequence of this invention, and may be isolated by methods known to those skilled in the art.

Detectable markers of this invention will be labelled with commonly employed radioactive labels, i.e. $^{32}P$, although other labels may be employed. The markers will be detected by autoradiographic, spectrophotometric or other means known in the art.

Methods to be used for the isolation of DNA and RNA for the practice of this invention are well known in the subject art (cf. ref. 13).

A method of determining the predisposition of a subject to a disease associated with a DNA sequence of this invention is presented. The method involves isolating the genomic DNA of a cell from the subject, contacting the DNA so isolated with a detectable marker which specifically binds to at least a portion of an activated oncogene of this invention and detecting the marker so bound. The presence of bound marker indicates a predisposition of the subject to the disease.

The detectable marker may be a labelled DNA sequence, including a labelled cDNA sequence, having a nucleotide sequence complimentary to at least a portion of the DNA sequence of this invention, produced by methods known to those skilled in the subject art.

The detectable marker may also be a labelled ribonucleotide (RNA) sequence having a nucleotide sequence complementary to at least a portion of the DNA sequence of this invention, and may be isolated by methods known to those skilled in the art.

Detectable markers of this invention will be labelled with commonly employed radioactive labels, i.e. $^{32}P$, although other labels may be employed. The markers will be detected by autoradiographic, spectrophotometric or other means known in the art.

A method of determining the predisposition of a subject to a disease is disclosed which comprises isolating the RNA from a cell from the subject, contacting the RNA so isolated with a detectable marker which specifically binds to at least a portion of the RNA encoded by an activated oncogene of this invention and detecting the marker so bound, the presence of bound marker indicating a predisposition of the subject to the disease.

The detectable marker may be a labelled DNA sequence, including a labelled cDNA sequence, having a nucleotide sequence complementary to at least a portion of the DNA sequence of this invention, produced by methods known to those skilled in the subject art.

The detectable marker may also be a labelled ribonucleotide (RNA) sequence having a nucleotide sequence complementary to at least a portion of the DNA sequence of this invention, and may be isolated by methods known to those skilled in the art.

Detectable markers of this invention will be labelled with commonly employed radioactive labels, i.e. $^{32}P$, although other labels may be employed. The markers will be detected by autoradiographic, spectrophotometric or other means known in the art.

A polypeptide molecule encoded by an activated oncogene is also provided by this invention. The polypeptide has the properties of transforming NIH3T3 cells and of inducing a tumor when injected into nude mice. The polypeptide has an amino acid sequence substantially as shown in FIGS. 3A and 3B.

The presently preferred polypeptide will be encoded by a mas oncogene, and will be expressed in a human, although the polypeptide may be expressed in a variety of other organisms.

The polypeptide of this invention may be obtained by synthetic means, i.e. chemical synthesis of the polypeptide from its component amino acids, by methods known to those skilled in the art. In the presently preferred embodiment, the polypeptide may be obtained by isolating it from cells expressing the mas gene, i.e. a cloned mas gene in a bacterial cell, or by in vitro translation of the mRNA encoded by the mas gene to produce the polypeptide of this invention. Techniques for the isolation of polypeptides by these means are well known to those skilled in the art.

A method of detecting a tumor cell is also provided. The method involves isolating a cell, contacting the cell with a detectable marker which binds specifically to at least a portion of a polypeptide of this invention and detecting the presence of marker bound to the cell. The presence of marker so bound indicates that the cell may be a tumor cell.

The detectable marker will preferably be a labelled immunoglobulin molecule, although other markers known in the art may be employed. The immunoglobulin molecule may be an antibody produced by contacting the immune system of an animal with at least a portion of the polypeptide of this invention, or with a synthetic amino acid sequence substantially similar to a portion of a polypeptide of this invention. The antibody molecule may also be produced by a combination of recombinant DNA techniques with other techniques known in the art.

Detectable markers of this invention will be commonly employed markers such as heavy metals, radioactive, e.g. $^{35}S$, fluorescent, e.g. fluorescein, or enzymatic, e.g. peroxidase. Detection of the labelled markers may be carried out by autoradiographic, spectrophotometric, or colorimetric techniques or by other methods known in the art.

A method for detecting a tumor in a subject is also presented. This method comprises contacting the tumor with a detectable marker which specifically binds at least a portion of a polypeptide of this invention and detecting the marker so bound. The presence of bound marker indicates the presence of a tumor.

A presently preferred method comprises introducing into the bloodstream of the patient a detectable amount of the marker such that the marker contacts and binds to a tumor expressing the polypeptide encoded by an activated oncogene, the tumor being detectable thereby.

The presently preferred marker is a labelled immunoglobulin molecule, although other markers known in the art may be employed. The immunoglobulin molecule may be an antibody produced by contacting the immune system of an animal with at least a portion of the polypeptide of this invention, or with a synthetic amino acid sequence substantially similar to a portion of a polypeptide of this invention. The antibody may also be produced by a combination of recombinant DNA techniques with other techniques known in the art.

Presently preferred labels for the antibody molecules are radioopaque labels, i.e. heavy metals, or enzymatic markers, known in the art.

A serum-based method for detecting a tumor in a subject is also presented. The method comprises isolating serum from the subject, contacting the serum with a first detectable marker which binds specifically to at least a portion of a polypeptide of this invention and detecting the marker so bound. The presence of bound marker indicates the presence of a tumor.

The first detectable marker is preferably a labelled antibody which may be free, i.e. in a solution, or may be bound to a matrix, i.e. a matrix such as polystyrene beads or the wall of a tube.

Presently preferred labels for the antibody molecule are radiolabels, i.e. $^{35}S$, heavy metals, or enzymatic labels. The bound antibodies will be detectable by autoradiography, scintillation counting or by colorimetry or by various other means.

The second detectable marker of this invention will also be a labelled antibody molecule and may specifically bind to the polypeptide or to the first marker or to a combination. The second marker will be labelled by radiolabels, heavy metals or enzymes, and detectable by means similar to those used to detect the first marker. The second marker may also be detectable by visual inspection if it causes precipitation of the first marker-polypeptide complex.

Finally, a method for treating in a subject a tumor induced by an activated mas oncogene is disclosed. The method comprises isolating an immunoglobulin molecule which specifically binds to at least a portion of a polypeptide encoded by the activated mas oncogene, attaching to the immunoglobulin molecule so isolated a substance which substantially limits the growth of a tumor or which destroys tumors to produce an antitumor immunoglobulin molecule, and contacting the tumor with an effective amount of the antitumor immunoglobulin molecule so produced, thereby limiting tumor growth or destroying the tumor.

The immunoglobulin molecule is preferably obtained by contacting the immune system of an animal with at least a portion of a polypeptide encoded by the associated mas oncogene, or with a synthetic amino acid sequence substantially similar to a portion of the polypeptide, to produce a specific antibody molecule, and isolating the antibody therefrom. The immunoglobulin molecule may also be produced by a combination of recombinant DNA techniques and other techniques known in the art.

Substances which substantially limit the growth of a tumor or which destroy tumors are known in the art, and may be molecules such as interferon, tumor necrosis factors, or radioactively labelled amino acids.

Materials and Methods

Focus and tumorigenicity assays

High molecular weight DNA was purified from cell lines (37) and solid tumors (14) as described. DNA transfer into NIH3T3 cells were performed by a modified calcium phosphate precipitation method (50). Focus assays (37) and tumorigenicity experiments (14) were performed as previously described. The plasmids pT24 (containing the activated human H-ras$^{val112}$ gene) and pKOneo (containing a neomycin/G418 antibiotic resistance gene) were previously described (13, 14).

Construction of libraries

Genomic libraries were constructed in the cosmid vector pHC79 (23, 33) from EcoRI partially cleaved DNA and were screened by colony filter hybridization (22). A cDNA library was constructed in lambda gt10 (25) from purified poly A+mRNA (33) from the MAS-133 cell line. The cDNA library was screened by plaque hybridization (52).

DNA analysis

Southern blots were performed as previously described (43). S1 mapping was done by a modification of the Berk-Sharp method (48). DNA sequences were determined in both orientations by the dideoxy method of Sanger et al. (40) as modified by Biggins et al. (2). DNA and protein homology searches were performed using a previously developed algorithm (18), and the Protein Identification Resource (National Biomedical Research Foundation, Georgetown University Medical Center, Washington, D.C.) and GENBANK (Bolt, Beranek and Newman, Inc., Cambridge, Mass.) data banks.

Results

Isolation of the mas oncogene

The mas oncogene was detected using the cotransfection and tumorigenicity assay as previously described (14). The mas gene was then isolated from cotransformed cells using established methods. DNA from a human epidermoid carcinoma was used to contransfect NIH3T3 cells with the plasmid pKOneo and transfected cells were selected with neomycin analog G418. In one experiment, one of the six nude mice injected with these cells developed a "primary" tumor within four weeks. Nude mice injected with cells contransfected with DNA isolated from this primary tumor developed "secondary" tumors within two weeks. After a third round, DNA was purified from a "tertiary" tumor and a genomic library was constructed in the cosmid vector pHC79. Four overlapping cosmid clones which contained human DNA were isolated by filter hybridization to total human genomic DNA (20, 42). Characterization of these cosmids by restriction mapping and Southern hybridization to total human DNA revealed that one of the cosmids, pMAS1, contains a 22 kbp stretch of human DNA flanked by mouse DNA on both sides (FIG. 1).

The pMAS1 cosmid was tested by the cotransfection and tumorigenicity assay to determine if it contained transforming potential. Nude mice developed tumors within two weeks after injection of cells which had been cotransformed with pMAS1 and pKOneo and selected for resistance to G418 (see Table 1). Furthermore, in our standard focus assay, NIH3T3 cells transfected with pMAS1 formed foci within 16 days. The foci of cells transformed with pMAS1 are unlike foci of cells transformed with the activated human H-ras$^{val112}$ oncogene, isolated from the T24 bladder carcinoma cell line. They appear at a lower frequency about 4-6 days later (Table 2). The foci induced by pMAS1 are characterized not by an abnormal morphology of the constituent cells, but by an exceedingly high cell density.

To define the regions of pMAS1 essential for transforming activity, various restrictions endonuclease digests of pMAS1 were tested by the NIH3T3 focus assay.

TABLE 1

| | TUMORIGENICITY ASSAYS | | | | | |
|---|---|---|---|---|---|---|
| | Mean tumor diameter (mm) after week: | | | | | |
| Test Plasmid | 1 | 2 | 3 | 4 | 5 | 6 |
| pMAS-1 | 0.0 | 11.1 | 19.6 | | | |
| | 0.0 | 9.8 | 16.0 | | | |
| | 0.0 | 10.9 | 17.0 | | | |
| | 0.0 | 10.6 | 18.0 | | | |
| pHM-2 | 0.0 | 0.0 | 4.5 | 10.6 | 11.2 | |
| | 0.0 | 0.0 | 5.4 | 10.6 | 14.0 | |
| | 0.0 | 0.0 | 0.0 | 5.8 | 13.6 | |
| | 0.0 | 0.0 | 0.0 | 8.7 | 13.7 | |
| | 0.0 | 0.0 | 0.0 | 0.0 | 5.0 | 9.8 |
| | 0.0 | 0.0 | 0.0 | 0.0 | 0.0 | 0.0 |
| None | 0.0 | 0.0 | 0.0 | 0.0 | 0.0 | 0.0 |
| | 0.0 | 0.0 | 0.0 | 0.0 | 0.0 | 0.0 |
| | 0.0 | 0.0 | 0.0 | 0.0 | 0.0 | 0.0 |
| | 0.0 | 0.0 | 0.0 | 0.0 | 0.0 | 0.0 |
| pT24 | 10.6 | 22.8 | | | | |
| | 9.0 | 22.8 | | | | |

Tumorigenicity assays were performed as previously described (14) (1984). NIH3T3 cells (8 × 10$^5$ cells/plate) were cotransformed with 200 ng pKOneo, 30 μg of high molecular weight NIH3T3 DNA and test plasmid (300 ng of pMAS1, 300 ng of pHM2, or 50 ng of pT24) per plate. Following transfection, cells were split 1:5 and selected for resistance to antibiotic G418. After 2 weeks the cells were confluent and were injected into nude mice (10$^7$ cells per mouse). Tumor formation at the site of injection was followed for six weeks and the mean tumor diameter was measured. Each line in the above table represents a single animal injected with independently cotransformed pools of cells.

When pMAS1 was cut with EcoRI or SalI the transforming potential was destroyed, indicating that regions including one or more of each of these sites are essential for transforming activity (Table 2). In contrast, pMAS1 DNA cut with SmaI or XhoI retained its transforming ability. A 7.3 kbp regions of pMAS1, which is defined by SmaI and XhoI sites and contains single EcoRI and SalI sites, is capable of transforming NIH3T3 cells. This regions was subcloned into pUC8 to generate pMS422 (FIG. 1).

Activation of the mas oncogene by rearrangement

Comparison of Southern blots of normal human DNA with DNA derived from the tertiary nude mouse tumor revealed a difference in the size and intensity of EcoRI restriction fragments homologous to mas suggesting that the mas gene was rearranged and amplified in transformants. To determine the nature of the DNA rearrangement, clones containing homology to a region of pMAS1 were isolated from a human placenta cosmid library. The probe used was the 2.2 kbp SalI-EcoRI restriction fragment which does not contain Alu-repetitive sequences and includes the 3' portion of the mas coding sequence (see next section). Three independent overlapping clones designated pHM1, pHM2 and pHM3 were obtained. Comparison of maps of restriction endonuclease sites in pHM2 and pMAS1 confirm that there is a break in homology localized between the EcoRI and HpaI sites in the 5' noncoding region of the mas gene (FIG. 1). Although this break point is not in the mas coding region (see next section), it does occur in a region essential for transformation of NIH3T3 cells by the mas gene (see above and Table 2). This suggests that the rearrangement found in the transformant is of functional significance.

TABLE II

| FOCUS ASSAYS | | | |
|---|---|---|---|
| Exp't A | DNA | ng/plate | foci/ng (2 wks.) |
| | pMAS1 | 200 | 0.105 |

TABLE II-continued
FOCUS ASSAYS

|  |  |  |  |
| --- | --- | --- | --- |
|  | pHM2 | 200 | <0.0025 |
|  | pHM2 | 1000 | <0.0005 |
|  | pT24 | 50 | 2.0 |
| Exp't B | DNA | ng/plate | foci/ng (3 wks.) |
|  | pMAS1 | 100 | 0.36 |
|  | pMAS1/SmaI | 100 | 0.41 |
|  | pMAS1/XhoI | 100 | 0.50 |
|  | pMAS1/EcoRI | 100 | <0.01 |
|  | pMAS1/SalI | 100 | <0.01 |
| Exp't C | DNA | ng/plate | foci/ng (3 wks.) |
|  | pMS422 | 400 | 0.61 |
|  | pMS424 | 400 | 0.50 |
|  | pGW34 | 400 | 0.60 |
|  | pHMS4 | 400 | <0.0001 |

Focus assays in NIH3T3 cells were performed as previously described (Perucho et al., 1981). NIH3T3 cells were transformed with the indicated amount of test DNAs, either cleaved with the indicated restriction enzymes (Exp't B), or uncleaved (Exp't A and Exp't C). High molecular weight NIH3T3 DNA (30 μg/plate) was used as carrier DNA. After the indicated times, the number of foci were scored and the number of foci/ng of test DNA was calculated. See FIG. 1 for a description of the plasmid clones.

The cosmid pHM2, which contains the normal human homolog of mas, was tested to determine if it has transforming activity. By the standard transfection assay described above, pHM2 did not induce foci of transformed NIH3T3 cells even after four weeks. However, pHM2 did induce tumors in a cotransfection and tumorigenicity assay, although with a longer lag time than pMAS1 (see Table 1). Therefore, the normal mas clones, pHM2, has a weak biological transforming activity detected by our tumorigenicity assays.

To test if the DNA rearrangement was responsible for activation of mas transforming potential, the hybrid clone pGW34 was constructed, which contains the 5' noncoding region of the rearranged gene and the entire coding region from the normal human homolog (see FIG. 1 and next section). This hybrid clone had focus inducing activity similar to the mas clone, pMS422 (Table 2). In contrast, pHMS4, a subclone of the normal placenta clone (FIG. 1), did not induce foci, suggesting that the DNA rearrangement is responsible for activation of mas transforming potential. Since this rearrangement lies outside of coding sequences, activation of the mas gene may result from overproduction or inappropriate production of its normal product. However, in order to make a definitive conclusion the nature of the normal gene transcript must be determined.

Finally, experiments were undertaken to determine if the mas gene was activated in the donor tumor DNA or, rather, became activated during cotransfection into NIH3T3 cells. Southern blotting experiments demonstrated that the mas genes resident in the original human epidermoid carcinoma did not have the rearranged structure found in the NIH3T3 cotransformant, nor were they amplified. Moreover, the transfer of the mas gene from the original tumor DNA has not been observed in other cotransformants. Thus, there is no evidence that the mas gene was active in the original human tumor. Rather, it is likely that the mas gene became rearranged and activated during gene transfer from the original human tumor DNA.

Organization and sequence of the mas gene transcript

Figure 2:
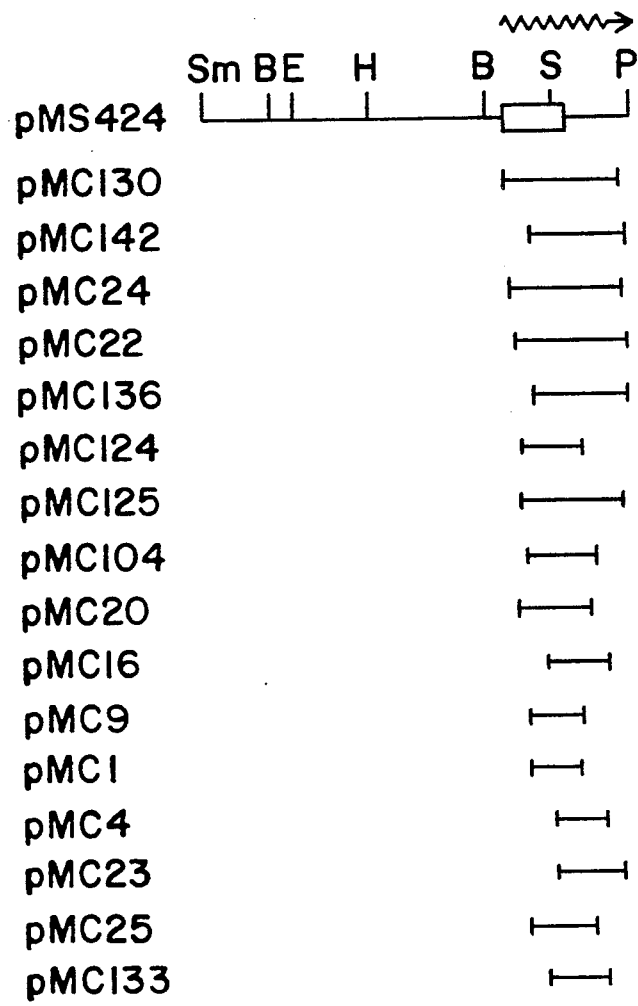
FIG. 2. Relation of mas cDNA clones to genomic clone pMS424. Inserts from the indicated cDNA clones are aligned under the genomic sequence. The open box indicates the coding region. The arrow shows the direction of transcription. Abbreviations for restriction endonuclease sites are as described in FIG. 1.

In order to define the transcription unit and coding potential of the mas gene, cDNAs complementary to mas mRNA were cloned. Poly A+ mRNA was purified from a cell line, MAS-133, derived from the nude mouse tumor from which pMAS1 was isolated. Blot hybridization of this RNA with the mas gene insert from pMS422 revealed a homologous mRNA approximately 2.5 kbp in length (data not shown). A cDNA library was constructed from this poly A+ RNA in the lambda gt10 vector and was screened for homology to pMS422. Sixteen overlapping cDNA clones were isolated and characterized by restriction endonuclease site mapping and DNA sequencing (see FIG. 2). From sequence data a composite nucleotide sequence was assembled which contains a complete open reading frame of 975 bp (FIGS. 3A and 3B). The first ATG in this reading frame is preceeded by an inframe stop codon at position -12. The entire open reading frame was contained on a single cDNA clones, pMC130. The orientation of transcription, as shown in FIG. 2 was postulated from this data.

Figure 4:
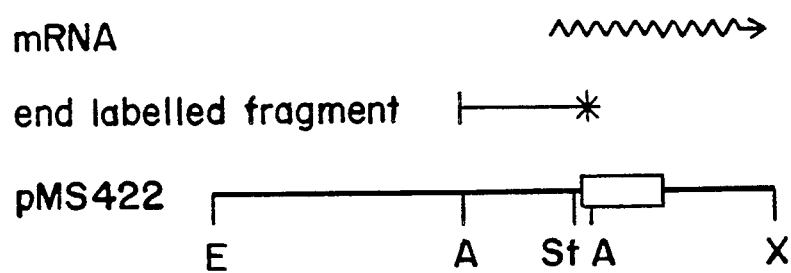
FIG. 4. S1 analysis of RNA transcripts. The AccI fragment of the genomic clone pMS422 was end-labelled and hybridized to RNA and digested with S1 nuclease. RNA used was isolated from NIH3T3 cells, MAS-133, or NIH3T3 cells transformed with the normal mas clone pHM2. Restriction endonuclease sites are indicated by the letters A (AccI), St (StuI), X (XhoI) and E (EcoRI). The StuI site is 10 bp 5' to the ATG initiation codon and includes the last base pair of the first inframe stop codon. This data indicates the colinearity between RNA transcripts and genomic sequences from the mas gene extend 5' beyond the termination codon at the StuI site.

Comparison of the restriction endonuclease cleavage sites of genomic and cDNA sequences indicated that the cDNA is entirely colinear with genomic sequences. This observation was subsequently confirmed for the coding region by direct nucleotide sequencing of the homologous region of the genomic DNA clone pMS422 (see FIGS. 3A and 3B). By the S1 analysis it was determined that the colinearity of the mRNA with the genomic DNA extends in the 5' direction approximately 45 bases beyond the first ATG in the coding region (FIG. 4). The site which marks the beginning of colinearity between RNA and genomic sequences may reflect a transcription initiation site or a splice site. Since no cDNA clones containing poly A were found, it is likely that mas transcripts extend beyond the 3' end of the cDNA clone pMC142 (see FIG. 2).

In order to learn more about the organization of the normal mas gene and the events which can lead to its activation, RNA was examined in cells which were cotransformed with the cosmid pHM2, selected from tumorigenicity in nude mice, and subsequently placed back into culture. Total RNA was prepared from these cells and analysed in the manner described for MAS-133 cells (see FIG. 4). This analysis indicates that transcripts of mas in these cells are also colinear with genomic DNA 5, to the open reading frame already Identified. Hence, the same protein is probably encoded in these cells as in MAS-133.

Predicted primary and secondary structure of the mas protein

Figure 5:
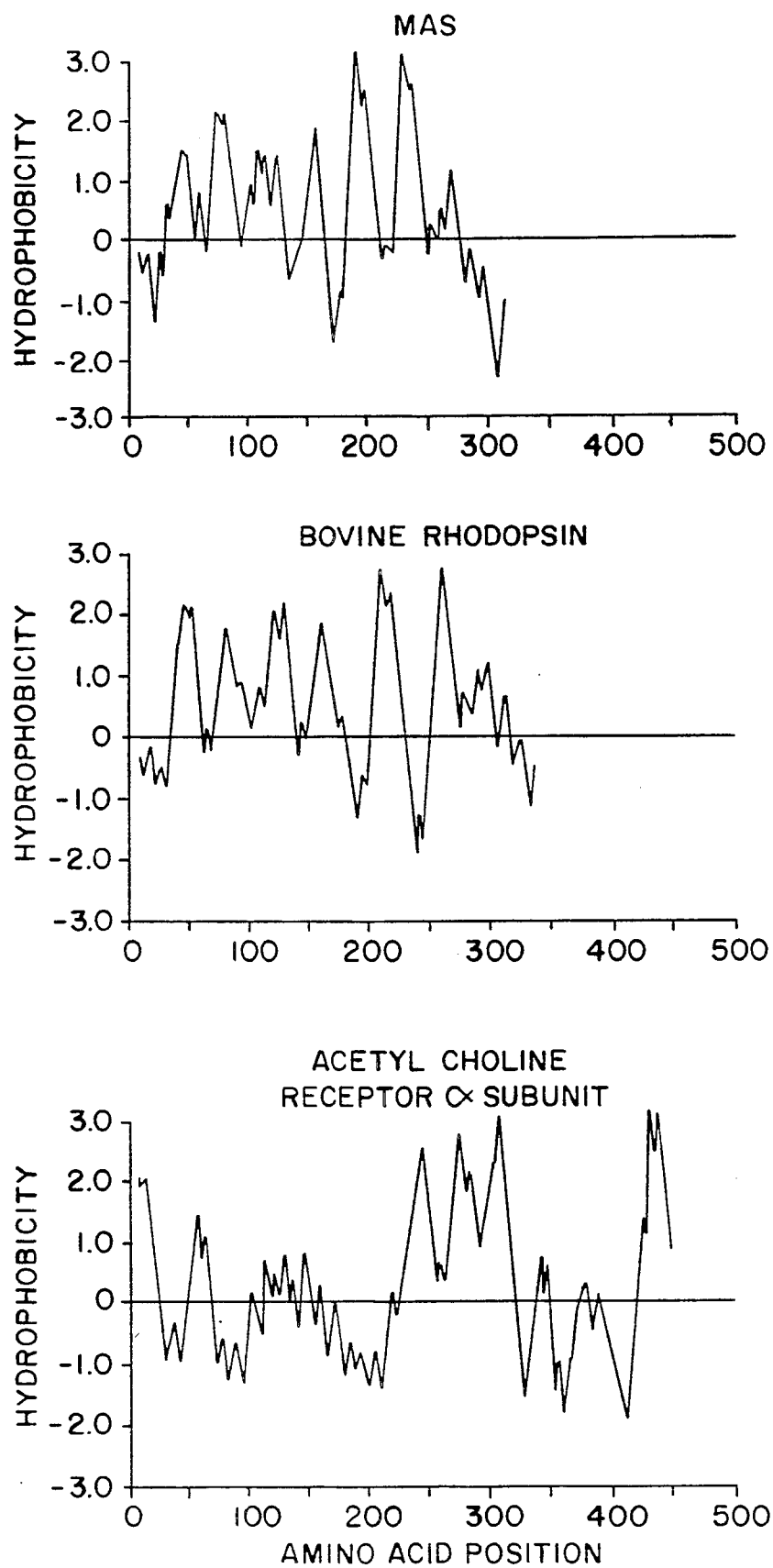
FIG. 5. Hydrochobicity plots of the predicted mas protein. Average hydrophobic values were determined for spans of 19 residues using the method and hydrophobic values of the Kyte and Doolittle (29). The plots of the predicted mas protein, bovine rhodopsin and the alpha subunit of acetlycholine receptor are shown for comparison.

The complete nucleotide sequence of the coding region determined from mas cDNAs and the corresponding predicted amino acid sequence of 325 amino acids are shown in FIGS. 3A and 3B. The deduced amino acid sequence does not share significant homology with any published sequence. Analysis of the hydrophobicity plot of the sequence by the method of Kyte and Doolittle (29) reveals that the mas protein has seven distinct hydrophobic regions (FIG. 5). Computational methods based on hydrophobicity profiles have been developed to distinguish transmembrane regions from hydrophobic internal regions of globular proteins (10). A recently developed algorithm correctly predicts membrane spanning segments in many proteins, including the seven segments in bacteriorhododpsin, and correctly disqualifies hydrophobic regions from many soluble proteins (11). This algorithm predicts seven transmembrane domains in the mas protein corresponding to the seven hydrophobic regions. Each of the hydrophobic regions are separated by hydrophilic regions which contain a predicted betaturn secondary structure (6). Both the amino and carboxy terminal ends of the mas protein are hydrophilic. This analysis strongly suggests that the mas protein is an integral membrane protein with many transmembrane domains.

Several proteins which span the membrane multiple times have been identified and studied. These include bacteriorhodopsin and the eucaryotic visual rhodopsins (36), lactose permease (16), the acetylcholine receptor (38), the sodium ion channel (35), the $(Na^++K^+)AT$-Pase (27,44), the $Ca^{2+}$-ATPase (32), and the erythrocyte anion exchange protein (26). In FIG. 5 the hydrophobicity plots of bovine rhodopsin and the alpha-subunit of acetlycholine receptor is shown for comparison with mas protein. There is a striking similarity in the hydrophobicity patterns of mas and rhodopsin, which may reflect structural and functional similarities in these proteins.

The mas protein does not contain an N-terminal hydrophobic signal sequence characteristic of many membrane proteins (49). However, some proteins with multiple transmembrane domains such as bovine rhodopsin, the erythrocyte anion exchange protein, and the sodium channel protein, lack amino-terminal signal sequences. In the first two cases, insertion into the membrane is cotranslational and requires internal signal sequences (5, 17). Since the mas protein does not contain an amino terminal hydrophobic signal sequence, its integration into the membrane may also depend on internal signal sequences or alternatively, it may spontaneously insert into the membrane due to its hydrophobic nature (4, 12).

It has been established that the tripeptide sequence Asn-X-Thr/Ser is a site for N-glycosylation in secreted and membrane proteins (28), although not all of these sequences are glycosylated (45). There are four potential sites for N-glycosylation in the predicted protein sequence of mas at positions 5, 16, 22 and 272. The first three of these sites are clustered in the first hydrophilic amino terminal region, while the fourth site is in the seventh hydrophobic domain.

Discussion

The cotransfection and tumorigenicity assay was developed to search for transforming genes from tumor cells which may not be readily detected by the standard focus assay. Using this assay, three transforming genes were previously isolated from MCF-7 cell line (14). One of these genes is a normal N-ras gene, which is amplified in MCF-7 DNA. Another, designated mcf2, is currently being investigated, and the third is the mcf 3 is the human homolog of v-ros (Birchmeier et al., manuscript in preparation). In the later case, the human ros gene was rearranged during or after gene transfer, probably resulting in its activation. A similar event appears to have occurred in the activation of the mas gene. The mas gene was found to be rearranged and amplified in the tertiary nude mouse tumor DNA. In contrast, the mas genes of the original human tumor DNA, used in the first round of cotransfection experiments, have the normal configuration and are not amplified. Although the normal human mas gene has weak tumor inducing activity, it has no detectable focus inducing activity. By contrast, the rearranged mas gene has strong tumor inducing activity and can induce foci of NIH3T3 cells. Analysis by chimeric gene construction indicates that a similar rearrangement can activate the normal placental allele. Therefore, it was concluded that the cotransfection and tumorigenicity assay has a propensity for detecting those proto-oncogenes which can induce tumorigenicity in NIH3T3 cells by arrangement and/or amplification following cotransfection. In this respect, the NIH3T3 cotransfection and tumorigenecity assay differs considerably from the NIH3T3 focus assay, which very rarely scores positive with DNA which does not already contain an activated oncogene.

It is not yet precisely understood how the mas gene became activated during gene transfer. In transformants, the mas gene has been rearranged, but this rearrangement does not appear to involve the coding domain. It is clear that the oncogenic potential of a normal placental allele can be activated by reconstructing a chimeric gene which replaces the normal 5' sequence with a sequence 5'. to the coding region of the rearranged gene. This chimeric gene leaves intact the long open reading frame of the placental allele. Thus it seems likely that transformation by mas results from inappropriate expression of a normal gene product. However, the possibility that the rearranged alleles have an altered splicing pattern which results in an altered protein product cannot be excluded. To completely resolve this problem mas transcripts in a normal cell must be identified. However, transcripts of the mas gene in cells cotransformed with the normal allele have been examined. Sl analysis indicates that in such cells we can exclude the existence of an additional N-terminal coding domain.

There are currently about 30 known viral or cellular oncogenes which code for proteins associated with the plasma membrane (30). Three oncogenes, v-erb-B, v-fms and v-ros code for proteins with single transmembrane domains and are probably related to growth factor receptors (9, 21, 34). While ras and src do not encode transmembrane domains, they are associated with the membrane and have fatty acid residues which are added to the proteins by a posttranslational modification (41, 8, 51). Most of these membrane associated oncoproteins, with the exception of the ras proteins, have tyrosine kinase activities which have been implicated in transformation (24). Although there is no direct proof that tyrosine phosphorylation is responsible for cellular transformation, there is a good correlation between the transforming abilities and tyrosine phosphorylation activities of viral transforming proteins.

In contrast to the structure of the membrane associated oncogene products discussed above, the structure of the mas gene product implied from the cDNA sequence is very different. A compute search through the Protein Identification Resource and GENBANK data bases (see Experimental Procedures) found no significant homology between mas and any known DNA or protein sequences, including protein kinases or ras proteins. The hydrophobicity plot of the amino acid sequence indicates that there are seven very hydrophobic regions which are potential transmembrane domains. This strongly suggests that the mas protein is an integral membrane protein which may cross the plasma membrane many times. Only one transforming gene has previously been described which encodes a protein with multiple transmembrane domains. This gene, encoded by the Epstein-Barr virus, codes for a plasma membrane protein (LMP) with six potential transmembrane domains (15) and has recently been shown to be capable of transforming Rat-1 cells (47). Unlike the mas protein, LMP has a long carboxy terminal hydrophilic region. Moreover, unlike the mas gene, the LMP gene does not render NIH3T3 cells tumorigenic.

While the structure of mas is unlike the canonical structure of the most of the known hormone receptors it is similar to a class of proteins which include the acetylcholine receptor and the visual rhodopsins. The acetylcholine receptor functions as a hormonally regulated ion channel. Visual rhodopsin is a light receptor which functions to activate transducin, an intracellular guanine nucleotide binding protein. The mas gene may encode a receptor which activates a critical component in a growth regulatory pathway, perhaps by serving in signal transduction or as a membrane channel. The unique nature of mas leads to the suspicion that it may provide a new link in understanding growth control.

References

1. Bargmann, C. I., M.-C. Hung and R. A. Weinberg (1986). The neu oncogene encodes an epidermal growth factor receptor-related protein. Nature 319: 226-230.
2. Biggin, M. D., T. J. Gibson and G. F. Hong (1983). Buffer gradient gels and 35S lable as an aid to rapid DNA sequence of determination. Proc. Natl. Acad. Sci. USA 80: 3963-3965.
3. Bishop, J.M. (1985). Viral oncogenes. Cell 42:23-38.
4. Blobel, G. (1980). Intracellular protein topogenesis. Proc. Natl. Acad. Sci. 77 1496-1500.
5. Braell, W. A. and H. F. Lodish (1982). The erythrocyte anion transport protein is cotranslationally insered into microsomes. Cell 28: 23-31.
6. Chou, P. Y. and G. D. Fasman (1978). Prediction of the secondary structure of proteins from their amino acid sequence. Adv. Enzymol. 47: 45-148.
7. Cooper, C. S., M. Park, D. G. Blair, M. A. Tainsky, K. Huebner, C. M. Croce and G. F. Van Woude (1984). Molecular cloning of a new transforming gene from a chemically transformed human cell line. Nature 311: 29-33.
8. Cross, F. R., E. A. Garber. D. Pellman and H. Hanafusa (1984). A short sequence in the p60-src N-terminus is required for p60-src myristylation and membrane association for cell transformation. Mol. Cell. Biol. 4: 1834-1842.
9. Downward, J., Y. Yarden, E. Mayes, G. Scrace, N. Totty, P. Stockwell, A. Ullrich, J. Schlessinger and M. D. Waterfield (1984). Close similarity of epidermal growth factor receptor and v-erb-B oncogene protein sequences. Nature 307: 521-527.
10. Eisenberg, D. (1984). Three-dimensional structure of membrane and surface proteins. Ann. Rev. Biochem. 53: 595-623.
11. Eisenberg, D., E. Schwarz, M. Komaromy and R. Wall (1984). Analysis of membrane and surface protein sequences with the hydrophobic moment plot. J. Mol. Biol. 179: 125-142.
12. Engelman, D. M. and T. A. Steitz (1981). The spontaneous insertion of proteins into and across membranes: the helical hairpin hypothesis. Cell 23: 411-422.
13. Fasano, O., E. Taparowsky, J. Fiddes, M. Wigler and M. Goldfarb (1983). Sequence and structure of the coding region of the human H-ras-1 gene from T24 bladder carcinoma cells. J. Molecular Applied Genetics 2: 173-180.
14. Fasano, O., Birnbaum, D., Edlund, L., Fogh, J. and M. Wigler (1984). New human transforming genes detected by a tumorigenicity assay. Mol. Cell. Biol. 4: 1695-1705.
15. Fennewald, S., V. van Santen and E. Kieff (1984). Nucleotide sequence of an mRNA transcribed in latent growth-transforming virus infection indicates that it may encode a membrane protein. J. Virol. 51: 411-419.
16. Foster, D. L., M. Boublik, and H. R. Kaback (1983). Structure of the lac carrier protein of E. coli. J. Biol. Chem. 258: 31-34.
17. Friedlander. M. and G. Bloberl (1985). Bovine opsin has more than one signal sequence. Nature 318: 338-343.
18. Goad, W. B. and Kanehisa, M. I. (1982). Pattern recognition in nucleic acid sequences. I. A general method for finding local homologies and symmetries. Nucl. Acids. Res. 10: 247-263.
19. Goubin, G., D. S. Goldman, J. Luce, P. E. Neiman and G. Cooper (1983). Molecular cloning and nucleotide sequence of a transforming gene detected by transfection of chicken B-cell lymphoma DNA. Nature 302: 114-119.
20. Gusella, J. F., C. Keys, A. Varsanyi-Breiner, F. Kao, C. Jones, T. T. Puck and D. Housman (1980). Isolation and localization of DNA segments from specific human chromosomes. Proc. Natl. Acad. Sci. 77: 2829:2833.
21. Hampe, A., M. Gobert, C. Sherr and F. Galibert (1984). Nucleotide sequence of the feline retroviral oncogene v-fms shows unexpected homology with oncogenes encoding tyrosine-specific protein kinases. Proc. Natl. Acad. Sci. 81: 85-89.
22. Hanahan, D and M. Meselson (1983). Plasmid screening at high colony density. Methods Enzymol. 100: 333-342.
23. Hohn, B. and J. Collins (1980). A small cosmid for efficient cloning of large DNA fragments. Gene 11: 291-298.
24. Hunter, T. and J. A. Cooper (in press). Viral oncogenes and tyrosine phosphorylation. In The Enzymes 'Enzyme Control by Phosphorylation'. eds. P. D. Boyer and E. G. Krebs, Academic Press, New York.
25. Huynh, T. V., R. A. Young and R. W. Davis (1984). Constructing and screening cDNA libraries in lambda gt10 and lambda gt11. In DNA Cloning Techniques: A Practical Approach, D. Glover, ed. IRL Press, Oxford.
26. Jay, D. and L. Cantley (1986). Structural aspects of the red cell anioon exchange protein. Ann. Rev. Biochem. (in press).
27. Kawakami, K., S. Noguchi, M. Noda, H. Takahashi, T. Ohta, M. Kawamura, H. Nojima, K. Nagano, T. Hirose, S. Inayama, H. Hayashida, T. Miyata and S. Numa (1985). Primary structure of the alpha-subunit of Torpedo californica (Na$^+$+K$^+$)ATPase deduced from cDNA sequence. Nature 316: 733-736.
28. Kornfeld, K. and S. Kornfeld (1985). Assembly of asparagine-linked oligosaccharides. Ann. Rev. Biochem. 54: 631-664.
29. Kyte, J. and R. F. Doolittle (1982). A simple method for displaying the hydropathic cancer of a protein. J. Mol. Biol. 157: 105-132.
30. Land, H , Parada, L. F. and R. A. Weinberg (1983). Cellular oncogenes and multistep carcinogenesis. Science 22: 771-778.
31. Lane, M. A., A. Sainten, K. M. Doherty and G. M. Cooper (1984). Isolation and characterization of a stage-specific transforming gene, Tlym-1, from T-cell lymphomas. Proc. Natl. Acad. Sci. 81: 2227-2231.
32. MacLennan, D. H., C. J. Brandl, B. Korczak and N. M. Green (1985). Amino-acid sequence of a $Ca^{2+} + Mg^{2+}$-dependent ATPase from rabbit muscle sarcoplasmic reticulum, deduced from its complementary DNA sequence. Nature 316: 696-700.
33. Maniatis, T., E. F. Fritsch and J. Sambrook (1982). Molecular Cloning: A Laboratory Manual. Cold Spring Harbor Laboratory, Cold Spring Harbor, N.Y.
34. Neckamyer, W. S. and L. H. Wang (1985). Nucleotide sequence of avian sarcoma virus UR2 and comparison of its transforming gene with other membrs of the tyrosine protein kinase oncogene family. J. Virol. 53: 879-884.
35. Noda, M., S. Shimizu, T. Tanabe, T. Takai, T. Kayano, T. Ikeda, H. Takahashi, H. Nakayama, Y. Kanaoka, N. Minamino, K. Kangawa, H. Matsuo, M. A. Ragery, T. Hirose, S. Inayama, H. Hayashida, T. Miyata and S. Numa (1984). Primary structure of electricus sodium channel deduced from cDNA sequence. Nature 312: 121-127.
36. Ovchinnikov, Y. A. (1982). Rhodopsin and bacteriorhodopsin: structure-function relationships. FEBS Letters 148: 179=191.
37. Perucho, M., M. Goldfarb, K. Shimizu, C. Lama, J. Fogh and M. Wiger (1981). Human-tumor-derived cell lines contain common and different transforming genes. Cell 27: 467-476.
38. Popot, J. and J. Changeux (1984). Nicotinic receptor of acetylcholine: structure of an oligomeric integral membrane protein. Physiol. Rev. 64: 1162-1239.
39. Ross, M. J., M. W. Klymkowsky, D. Agard and R. M. Stroud (1977). Structural studies of a membrane-bound acetylcholine receptor from Toperdo californica. J. Mol. Biol. 116: 635-659.
40. Sanger, F., S. Nicklen and A. R. Coulson (1977). DNA sequencing with chain-terminating inhibitors. Proc. Natl. Acad. Sci. USA 74: 5463-5467.
41. Sefton, B. M., I. S. Trowbridge, J. S. Cooper and E. M. Scolnick (1982). The transforming proteins of Rous sarcoma virus, Harvey sarcoma virus and Abelson virus contain tightly bound lipid. Cell 31: 465-474.
42. Shih, C. and R. A. Weinberg (1982). Isolation of a transforming sequence from a human bladder carcinoma virus, Harvey sarcoma virus and Abelson virus contain tightly bound lipid. Cell 31: 465-474.
42. Shih, C. and R. A. Weinberg (1982). Isolation of a transforming sequence from a human bladder carcinoma cell line. Cell 29: 161-169.
43. Shimizu, K., M. Goldfarb, Y. Suard, M. Perucho, Y. Li, T. Kamata, J. Ferimisco, E. Stavnezer, J. Fogh and M. Wigler (1983). Three human transforming genes are related to the viral ras oncogenes. Proc. Natl. Acad. Sci. 802: 2112-2116.
44. Shull, G. E., A. Schwartz and J. B. Lingrel (1985). Amino-acid sequence of the catalytic subunit of the $(Na^+ + K^+)$ ATPase deduced from a complementary DNA. Nature 316: 691-695.
45. Struck, D. K. and W. J. Lennarz (1980). The function of saccharide-lipids in synthesis of glycoproteins. In The Biochemistry of Glycoproteins and Proteoglycans, ed. W. Lennarz, pp. 35-83. New York, Plenum.
46. Takahashi, M., J. Ritz and G. M. Cooper (1985). Activation of a novel human transforming gene, ret, by DNA rearrangement. Cell 42: 581-588.
47. Wang, D., D. Liebowitz and E. Kieff (1985). An EBV membrane protein expressed in immortalized lymphocytes transforms
48. Weaver, R. F. and C. Weismman (1979). Mapping of RNA by a modification of the Berk-Sharp procedure: the 5' termini of 15S beta-globin mRNA precursor and mature 10S beta-glovin mRNA have identical map coordinates. Nucl. Acids. Res. 7: 1175-1193.
49. Wicker, W. T. and H. F. Lodish (1985). Multiple mechanisms of protein insertion into and across membranes. Science 230: 400-407.
50. Wigler, M. M. R. Sweet, G. K. Sim, B. Wold, A. Pellicer, E. Lacy, T. Maniatis, S. Silverstein and R. Axel (1979). Transformation of mammalian cells with genes from procaryotes and eucaryotes. Cell 16: 777-785.
51. Willumsen, B. M., Christensen, N. L. Hubbert, A. G. Papageorige and D. R. Lowy (1984). The p21 ras C-terminus is required for transformation and membrane association. Nature 310: 583-586.
52. Woo, S. L. C. (1979). A sensitive and rappid method for recombinant phage screening. Methods Enzymol. 63: 389-395.

What is claimed is:

1. A method of detecting a tumor cell which comprises isolating a cell, contacting the cell with a detectable marker which binds specifically to at least a portion of a polypeptide molecule encoded by an activated oncogene, said molecule having the properties of transforming NIH3T3 cells, inducing a tumor when injected into nude mice, and further said polypeptide having an amino acid sequence substantially as shown in FIGS. 3A and 3B and detecting the presence of marker bound to the cell.

2. A method of claim 1, wherein the detectable marker is a labelled immunoglobulin molecule.

3. A method of claim 2, wherein the labelled immunoglobulin is labeled with a radionucleotide.

4. A method of claim 2, wherein the labelled immunoglobulin is labelled with an enzyme.

5. A method of claim 1, wherein the detecting is by autoradiography.

6. A method of claim 1, wherein the detecting is by spectrophotometry.

7. A method of claim 6, wherein the detecting is by colorimetry.

8. A method for detecting a tumor in a subject which comprises contacting the tumor with a detectable marker which specifically encoded by an activated oncogene, said molecule having the properties of transforming NIH3T3 cells, inducing a tumor when injected into nude mice, and further said polypeptide having an amino acid sequence substantially as shown in FIGS. 3A and 3B, and detecting the marker so bound.

9. A method of claim 8, wherein the subject is a human.

10. A method of claim 8, wherein the detectable marker is a labelled immunoglobulin molecule.

11. A method of claim 10, wherein the immunogobuin is labeled with a radioactive substance.

12. A method of claim 10, wherein the immunoglobulin is labelled with a heavy metal substance.

13. A method of claim 10, wherein the immunoglobulin is labelled with an enzyme.

14. A method for detecting a tumor in a subject which comprises isolating serum from the subject, contacting the serum with a first detectable marker which binds specifically to at least a portion of a polypeptide molecule encoded by an activated oncogene, said molecule having the properties of transforming NIH3T3 cells, inducing a tumor when injected into nude mice, and further said polypeptide having an amino acid sequence substantially as shown in FIGS. 3A and 3B to form a first marker-polypeptide complex and detecting the marker so bound.

15. A method of claim 14, wherein the detectable marker is a labelled immunoglobulin molecule.

16. A method of claim 15, wherein the immunoglobuin is labelled with a radioactive substance.

17. A method of claim 14, wherein the second detectable marker which specifically binds to at least a portion of the polypeptide is contacted with the first marker-polypeptide complex.

18. A method of claim 14, wherein the second detectable marker which specifically binds to at least a portion of the first marker is contacted with the first marker-polypeptide complex.

19. A method of determining the predisposition of a subject to a disease associated with a DNA sequence comprising an activated oncogene, which comprises isolating serum from the subject, contacting the serum with a first detectable marker which binds specifically to at least a portion of a polypeptide molecule encoded by the activated oncogene, said molecule having the properties of transforming NIH3T3 cells, inducing a tumor when injected into nude mice, and further said polypeptide having an amino acid sequence substantially as shown in FIG. 3 to form a first marker-polypeptide complex and detecting the marker so bound.

20. A method of claim 19, wherein the subject is a human.

21. A method of claim 19, wherein the detectable marker is a labelled immunoglobulin molecule.

22. A method of claim 19, wherein a second detectable marker which specifically binds to at least a portion of the polypeptide is contacted with the first marker polypeptide complex.

23. A method of claim 19, wherein a second detectable marker which specifically binds to at least a portion of the first marker is contacted with the first marker polypeptide complex.

* * * * *